United States Patent [19]
Carmen et al.

[11] Patent Number: 5,236,716
[45] Date of Patent: Aug. 17, 1993

[54] PLATELETS CONCENTRATE WITH LOW WHITE BLOOD CELLS CONTENT

[75] Inventors: Raleigh A. Carmen, Concord; Edward J. Nelson, San Rafael, both of Calif.

[73] Assignee: Miles Inc., Elkhart, Ind.

[21] Appl. No.: 836,631

[22] Filed: Feb. 14, 1992

Related U.S. Application Data

[62] Division of Ser. No. 478,853, Feb. 12, 1992, Pat. No. 5,089,146.

[51] Int. Cl.$^5$ .............................................. A61K 35/12
[52] U.S. Cl. ........................................ 424/532; 435/2; 210/782
[58] Field of Search ............... 210/206, 767, 782, 806, 210/787, 698, 781, 257.1, 645, 782; 424/532; 604/406, 408, 410; 435/2

[56] References Cited

U.S. PATENT DOCUMENTS

| | | | |
|---|---|---|---|
| 3,729,947 | 5/1973 | Higuchi | 424/532 |
| 4,280,497 | 7/1981 | Warner et al. | 604/408 |
| 4,344,560 | 8/1982 | Iriguchi et al. | 210/787 |
| 4,447,415 | 5/1984 | Rock et al. | 424/532 |
| 4,596,657 | 6/1986 | Wisdom | 210/206 |
| 4,695,460 | 9/1987 | Holme | 424/532 |
| 4,767,541 | 8/1988 | Wisdom | 210/787 |
| 4,855,063 | 8/1989 | Carmen et al. | 210/749 |
| 4,880,548 | 11/1989 | Pall et al. | 210/767 |
| 4,943,287 | 7/1990 | Carmen | 210/206 |
| 4,985,153 | 1/1991 | Kuroda et al. | 604/406 |
| 4,992,363 | 2/1991 | Murphy | 424/532 |
| 5,089,146 | 2/1992 | Carmen et al. | 210/782 |
| 5,104,788 | 4/1992 | Carmen et al. | 210/782 |

*Primary Examiner*—Robert A. Dawson
*Assistant Examiner*—Ana M. Fortuna
*Attorney, Agent, or Firm*—James A. Giblin; Elizabeth F. Enayati

[57] ABSTRACT

Platelet concentrate containing less then $10^6$ white blood cells and prepared from a unit of whole blood sample in a closed multiple blood bag system within less than about eight hours after the whole blood is removed from a human. The concentrate is contained in a platelet storage bag made from polyvinyl chloride plasticized with either trioctyltrimellitate or ethylene vinyl acetate.

3 Claims, 1 Drawing Sheet

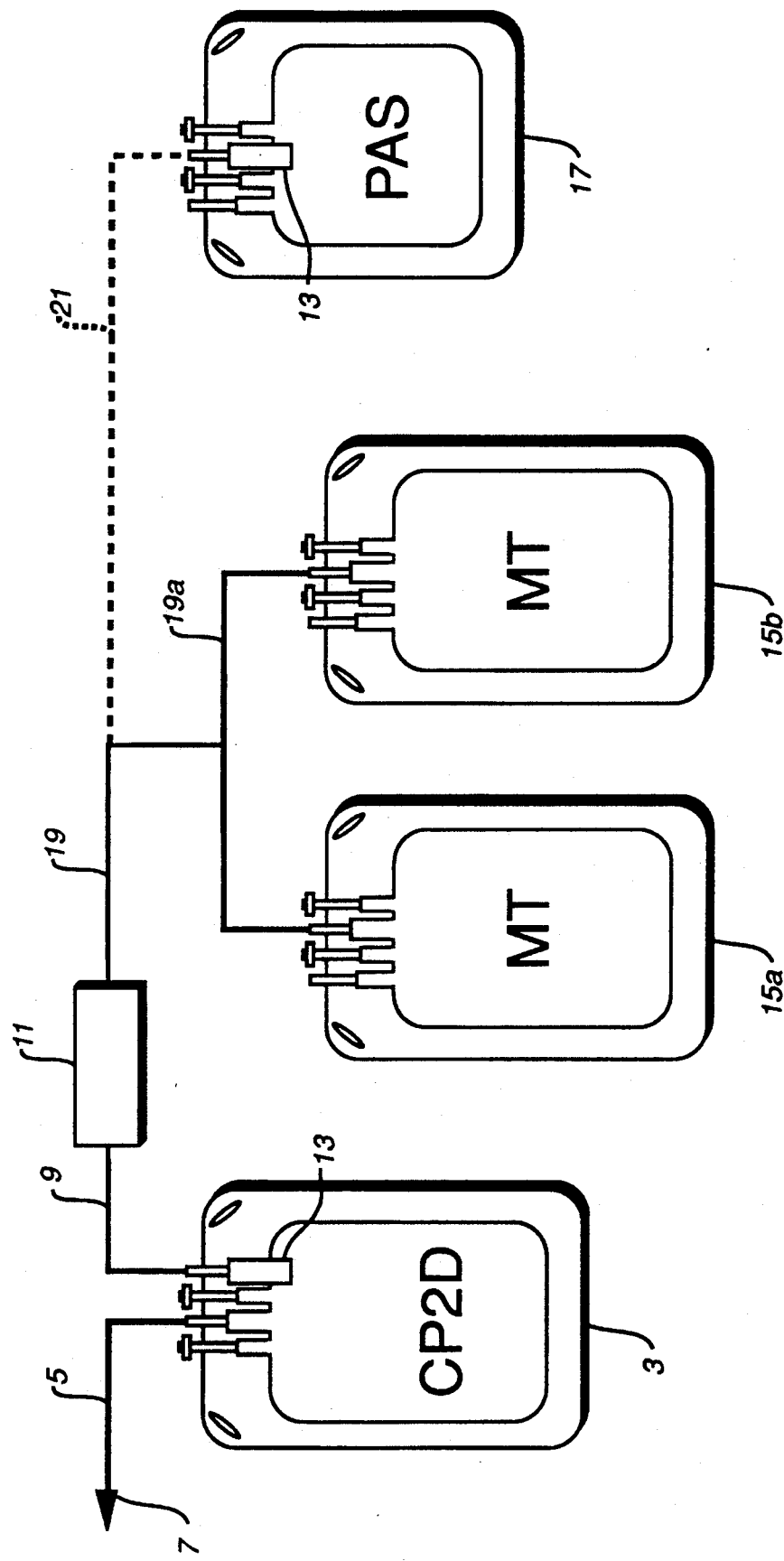

PLATELETS CONCENTRATE WITH LOW WHITE BLOOD CELLS CONTENT

This application is division, of application Ser. No. 07/478,853, filed Feb. 12, 1992, now U.S. Pat. No. 5,089,146.

BACKGROUND OF THE INVENTION

1. Field

This disclosure is concerned generally with the filtration of blood products and specifically with the filtration of white blood cells from platelets.

2. Prior Art

The advantages of removing white blood cells (WBCs) from blood components such as red blood cells (RBCs) and platelets are known. See, for example, U.S. Pat. No. 4,596,657 to Wisdom (removal of WBCs from RBCs). The removal of WBCs from platelets is disclosed in U.S. Pat. No. 4,857,190 to Kuhlemann et al. and in articles by Sirchia, G., et al., Vox Sang. 44:115-120, 1983, and Kickler, T. S. et al., Transfusion 29:411-414, 1989.

Existing methods remove WBCs from the final form of platelet concentrates (PC) or pools of such concentrates. See the Kuhlemann et al. patent which describes a platelet pooling bag designed for this purpose. Sirchia et al. disclose WBC removal after storage of a PC. Kickler et al. disclose filtration of a PC at the bedside, just before infusion into a patient. Before these existing methods can be used, however, the PC must be available. Unfortunately, the collection and initial processing of whole blood from a donor may result in a delay in the preparation of PCs.

In current practice at least two centrifugation steps are used to make a PC from whole blood. In the first step whole blood is collected in a blood bag and then centrifuged to form a lower, dense portion of RBCs and an upper, less dense portion of plasma which is rich in platelets and known as platelet rich plasma (PRP). The upper PRP is then expressed from the bag into a second bag which is centrifuged to form a lower, denser platelet pellet and an upper, less dense plasma portion known as platelet-poor plasma (PPP). The upper PPP is then expressed from the second bag for use in preparing various plasma products (e.g. albumin, immunoglobulins, coagulation factors and the like) leaving behind the plasma pellet or PC.

Even after the PC is made, however, it may be stored for some time (e.g., up to 5 days) before it is filtered to remove WBCs.

The presence of WBCs in a stored PC is thought to result in WBC degradation products that can adversely affect the platelets and their environment. Unfortunately, in conventional blood banking processes, there have been no available means for pre-storage removal of WBCs from platelets in a closed system. Thus, PCs, if filtered at all, have commonly been filtered just prior to infusion into the patient.

We have found that it is now possible to remove substantially all WBC's from a platelet product prior to platelet storage. This is done by filtering platelet rich plasma (PRP), preferably soon after it is formed from centrifuged whole blood, using the novel closed system described below. In a preferred embodiment the filtration of WBCs from the PRP occurs within 8 hours of whole blood collection from a donor.

SUMMARY OF THE INVENTION

Our method of preparing platelets that are substantially free of WBCs requires the removal of WBCs from a platelet rich plasma (PRP) prior to forming a platelet concentrate (PC) and prior to any extended PC storage (e.g. 5 days). The method comprises the steps of collecting whole blood from a donor into a donor blood bag, centrifuging the whole blood to form a lower level of packed red blood cells and an upper level of PRP, and then passing the PRP into a satellite bag through a filter capable of removing substantially all WBCs from the PRP. All of the steps are accomplished in a closed system. Examples of "closed" blood bag systems are well known. See, for example, U.S. Pat. No. 4,586,928 to Barnes et al.

In preferred embodiments, the PRP is filtered as soon as possible or at least within about 8 hours of a whole blood donation using a closed system comprising a WBC filter disposed between a donor bag and at least two communicating satellite bags. The system may preferably include a third satellite bag containing a platelet preservative (or additive) solution. Such solutions are well known. See, for example, U.S. Pat. No. 4,447,415 to G. Rock et al. and U.S. Pat. No. 4,695,460 to S. Holme. The third satellite bag (with additive solution) may be a part of the original closed system or added to the system later via sterile docking techniques to maintain a "closed" system. Examples of such sterile docking techniques are well known. See, for example, U.S. Pat. No. 4,507,119 and U.S. Pat. No. 4,443,215.

BRIEF DESCRIPTION OF THE FIGURE

The figure is a plan view of a preferred closed system for removal of WBCs from PRP soon after donation and centrifugation of whole blood.

SPECIFIC EMBODIMENTS

Our pre-storage filtration of platelets preferably uses a closed system such as that shown in the FIGURE. The FIGURE shows a donor bag 3 which may include a conventional anticoagulant solution such as CP2D, attached phlebotomy tubing 5 and needle 7 (illustrated by the arrow) connected via tubing 9 to an inlet port of WBC filter 11. Preferably, a valve such as frangible valve 13 (such as that shown in U.S. Pat. No. 4,586,928 to Barnes et al.) seals the contents of bag 3 until after bag 3 is centrifuged.

In closed communication with filter 11 via tubing 19 are at least two empty (MT) secondary (satellite) bags, 15*a* and 15*b*. In very preferred embodiments, a third satellite bag containing platelet additive solution (PAS) 17 is attached to the closed system via conventional blood bag tubing 21. Other bags may be added to the closed system for added uses.

In use, whole blood is collected from a donor using phlebotomy needle 7 to draw the blood into bag 3. The whole blood in bag 3 is then centrifuged using conventional methods to form an upper (less dense) platelet rich plasma (PRP) portion and a lower (more dense) packed red blood cell (RBC) portion. Then, valve 13 is opened and the PRP is expressed from bag 3 through filter 11 under conditions sufficient to remove WBCs and allow substantially all (more than 90%, preferably more than 99.5%) of the platelets to pass into one of the bags, 15*a* or 15*b*.

After the filtered PRP is collected into one of bags 15 via tubing 19, the donor bag 3 and filter 11 may be removed from the system by known means such as by cutting and sealing along tubing 19. The PRP in one of the bags, 15a, is then centrifuged to form a lower, denser platelet pellet and an upper, less dense platelet poor plasma (PPP) most of which can be expressed from the first satellite bag 15a to second satellite bag 15b via tubing 19a. Commonly, about 50 ml of residual plasma is left with the platelet pellet as a storage medium. At this point the second bag 15b containing the PPP can be removed from the system by cutting and sealing the connecting tubing 19a. This removed PPP can then be pooled with other PPP and used for other purposes such as plasma fractionation to produce useful blood components such as albumin, immunoglobulins, coagulation factors and the like.

At this point the platelet pellet remaining in bag 15a is resuspended in the residual plasma and is ready for use or storage for a period that can be up to five days.

To enhance storage, a platelet storage solution 17 from additional bag 21 can be added to bag 15. Examples of such solutions can be found in the above-cited patents to G. Rock et al and S. Holme. The disclosures of both patents are incorporated herein by reference to them.

Examples of preferred WBC filters then can be used in the above system are shown in U.S. Pat. No. 4,855,063 to Carmen et al. and U.S. Pat. No. 4,596,657 to Wisdom, the disclosures of which are also incorporated into this disclosure.

The tubings may be made from conventional polyvinyl chloride (PVC) blood tubing and the bags themselves are preferably made from plastic materials suited for their ultimate use. For example, in the case of platelet storage, the storage bags should have a high $O_2$/$CO_2$ gas transmissivity to control platelet pH. This can be accomplished using PVC film plasticized with trioctyltrimellitate (TOTM) as in U.S. Pat. No. 4,280,497 to Warner et al. or by using an ethylene vinyl acetate film. The donor bag may be made with the same plastic film or a different one more suitable for red blood cell storage (e.g. TOTM or, perhaps, DEHP plasticized PVC).

Specific examples and data are discussed below.

EXAMPLES

Three units of whole blood were collected into conventional donor blood bags. These bags were then centrifuged to separate PRP from red cells. Each unit of PRP was connected via conventional blood bag tubing to a WBC filter and expressed through the inline WBC filter (PL 100, available from Pall Corporation) into an attached blood bag similar to that of empty (MT) bag 15a of the FIGURE. The bag was made from a film of TOTM plasticized PVC of the type described in U.S. Pat. No. 4,280,497 to Warner et al. Before (and after) filtration leukocyte counts were:

TABLE I

| Unit No. | Before No × $10^8$ | After No × $10^8$ | % Removed |
|---|---|---|---|
| 272 | 0.47 | 0.005 | 98.9 |
| 273 | 1.81 | 0.009 | 99.5 |
| 274 | 1.52 | 0.005 | 99.7 |

After filtration, PRP units were processed via further centrifugation to PCs which were stored at 22° C. on an agitator. In vitro data (means values) in the table below show that pH was well maintained, platelets were consuming oxygen, morphology and hypotonic stress recovery were well maintained and there was no change in platelet number.

TABLE II

| | Day 1 | Day 4 | Day 5 | Day 6 | Day 7 |
|---|---|---|---|---|---|
| pH | 7.472 | 7.532 | 7.497 | 7.436 | 7.244 |
| $PCO_2$, mmHg | 20.0 | 12.2 | 11.7 | 11.2 | 14.8 |
| $PO_2$, mmHg | 52.0 | 61.7 | 71.7 | 78.6 | 52.9 |
| $HCO_3^-$, mM | 17.8 | 12.1 | 11.0 | 9.3 | 7.4 |
| % Discs, NAPSAC* | 36.3 | 43.6 | 35.6 | 29.3 | 20.6 |
| Hypotonic stress recovery, % | 58.6 | 58.2 | 54.7 | 49.2 | — |
| Platelets, No. × $10^{10}$ | 5.1 | 5.2 | 5.2 | 5.2 | 5.1 |

*Non-Invasive Assessment of Platelet Shape and Function (NAPSAC) machine described in more detail in U.S. Pat. No. 4,522,494 to R. F. Bonner and available from Beecher Medical, Silver Spring, MD. See also, U.S. Pat. 4,753,797 to Garcez which describes the use of NAPSAC.

As used herein, the substantial removal of all WBCs means that at least 95% of the original WBCs are removed. In very preferred embodiments, at least 99.5% of the original WBCs are removed from the PRP.

Substantially all original platelets means at least 90% of the original platelets remain after the filtration step to be recovered in the platelet storage bag attached to the filter (or less than 10% of the platelets remain in the WBC filter).

The system of the figure can be modified as follows for alternate applications for filtration after the platelet concentrate has been made:

1. The filter 11 can be placed in line 21 such that after the platelets are concentrated in bag 15a, and all the platelet poor plasma has been transferred to bag 15b, the PAS is then transferred through the filter into the platelet pellet. Following resuspension, the platelet concentrate is then transferred back through the filter into bag 17 where the WBC-poor platelet concentrate will be stored.

2. If no platelet additive is in the system, the filter 11 can be placed in line 19a attached to a third MT bag (not shown). Following concentration of the platelets in bag 15a, most of the platelet poor plasma is transferred into MT bag 15b, with about 50 ml of plasma remaining with the platelet pellet. Following resuspension of the platelets in the plasma, the platelet concentrate is transferred through the filter into the third MT bag in which it is stored.

Given the above disclosure, it is thought that numerous variations will occur to those skilled in the art. Accordingly, it is intended that the above examples should be construed as illustrative only and that the scope of the invention should be limited only by the following claims.

I claim:

1. A platelet concentrate containing less than $10^6$ white blood cells and prepared from a unit of whole blood sample in a closed multiple blood bag system less than about eight hours after the whole blood is removed from a human, the concentrate being contained in a platelet storage bag made from polyvinyl chloride plasticized with one from the group of plasticizers consisting of trioctyltrimellitate and ethylene vinyl acetate.

2. The platelet concentrate of claim 1 further comprising residual plasma from the whole blood in an amount effective for storing the platelets.

3. The platelet concentrate of claim 1 further comprising a platelet additive solution in an amount effective for storing the platelets.

* * * * *